US008742371B2

(12) United States Patent
Yamamoto et al.

(10) Patent No.: US 8,742,371 B2
(45) Date of Patent: Jun. 3, 2014

(54) METHOD FOR GENERATING OPTICAL TOMOGRAPHIC INFORMATION, OPTICAL TOMOGRAPHIC INFORMATION GENERATING APPARATUS, AND STORAGE MEDIUM

(75) Inventors: Hiroaki Yamamoto, Kanagawa (JP); Yukio Yamada, Tokyo (JP); Shinpei Okawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 306 days.

(21) Appl. No.: 13/145,564

(22) PCT Filed: Feb. 1, 2010

(86) PCT No.: PCT/JP2010/051348
§ 371 (c)(1),
(2), (4) Date: Jul. 21, 2011

(87) PCT Pub. No.: WO2010/087478
PCT Pub. Date: Aug. 5, 2010

(65) Prior Publication Data
US 2011/0272597 A1  Nov. 10, 2011

(30) Foreign Application Priority Data

Jan. 30, 2009  (JP) ................................ 2009-020330

(51) Int. Cl.
*G01N 21/64* (2006.01)
(52) U.S. Cl.
USPC .................. 250/459.1; 250/363.04
(58) Field of Classification Search
USPC ..................................................... 250/459.1
See application file for complete search history.

(56) References Cited

U.S. PATENT DOCUMENTS 6,615,063 B1  9/2003  Ntziachristos et al.
6,785,641 B1  8/2004  Huang
(Continued)

FOREIGN PATENT DOCUMENTS

JP  05-223738 A  8/1993
JP  11-173976 A  7/1999
(Continued)

OTHER PUBLICATIONS

S.R. Arridge, "Optical Tomography in Medical Imaging", Inverse Problems 15(1999) R41-93.
(Continued)

*Primary Examiner* — David Porta
*Assistant Examiner* — Djura Malevic
(74) *Attorney, Agent, or Firm* — SOLARIS Intellectual Property Group, PLLC

(57) ABSTRACT

Measurement data of intensities of fluorescence obtained by directing excitation light onto a subject is acquired. An initial value of an absorption coefficient of the phosphor is set on the basis of a concentration distribution of the phosphor, an intensity distribution of the fluorescence on the basis of an absorption coefficient and a diffusion coefficient (reduced scattering coefficient) of the subject, which are set beforehand, are calculated, and the measurement data is compared with the calculation result. If these are found not to be matched, an absorption coefficient of the phosphor at which the error will be a minimum is estimated by performing an inverse problem calculation using a mathematical model. The calculation of the intensity distribution of the fluorescence and evaluation of the error from the obtained concentration distribution are repeated using the absorption coefficient, and a concentration distribution for which the error is the minimum is acquired.

6 Claims, 6 Drawing Sheets

(56) References Cited

U.S. PATENT DOCUMENTS

| | | | |
|---|---|---|---|
| 7,107,116 B2* | 9/2006 | Geng | 700/117 |
| 7,242,997 B2* | 7/2007 | Geng | 700/117 |
| 7,383,076 B2* | 6/2008 | Ntziachristos et al. | 600/473 |
| 7,474,398 B2* | 1/2009 | Nilson et al. | 356/317 |
| 7,675,044 B2* | 3/2010 | Laidevant et al. | 250/458.1 |
| 8,190,241 B2* | 5/2012 | Ntziachristos et al. | 600/473 |
| 2004/0015062 A1 | 1/2004 | Vernet | |
| 2006/0203243 A1* | 9/2006 | Nilson et al. | 356/417 |
| 2007/0286468 A1 | 12/2007 | Joshi et al. | |
| 2008/0031494 A1* | 2/2008 | Rice et al. | 382/110 |
| 2008/0219933 A1* | 9/2008 | Ntziachristos et al. | 424/9.6 |
| 2009/0184259 A1* | 7/2009 | Ma et al. | 250/483.1 |
| 2010/0224797 A1* | 9/2010 | Laidevant et al. | 250/459.1 |
| 2010/0256496 A1* | 10/2010 | Zhu | 600/459 |
| 2012/0025101 A1* | 2/2012 | Ma et al. | 250/459.1 |

FOREIGN PATENT DOCUMENTS

| | | |
|---|---|---|
| JP | 11-337476 A | 12/1999 |
| JP | 2004-514150 A | 5/2004 |
| JP | 2004-514150 T | 5/2004 |
| JP | 2006-026017 A | 2/2006 |
| JP | 2008-149154 A | 7/2008 |
| JP | 2008-537995 A | 10/2008 |
| JP | 2008-537995 T | 10/2008 |

OTHER PUBLICATIONS

Japanese Office Action dated Sep. 4, 2012, issued in the corresponding to Japanese Patent Application.

Extended European search report dated Apr. 26, 2013 from the EPO in European patent application corresponding to the instant patent application.

* cited by examiner

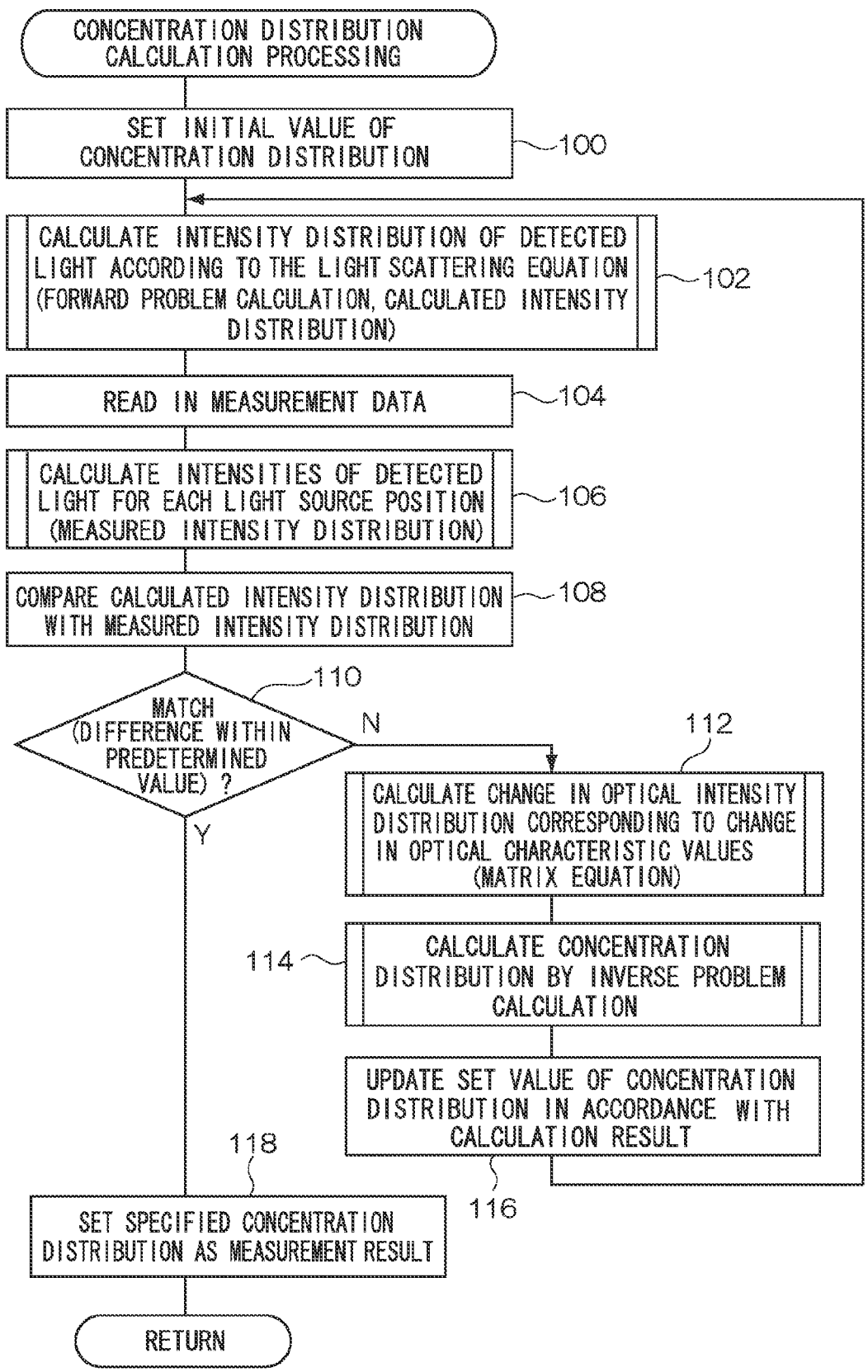

METHOD FOR GENERATING OPTICAL TOMOGRAPHIC INFORMATION, OPTICAL TOMOGRAPHIC INFORMATION GENERATING APPARATUS, AND STORAGE MEDIUM

TECHNICAL FIELD

The present invention relates to using light for tomography, and more particularly relates to a method for generating optical tomographic information that illuminates excitation light and may acquire optical tomographic images containing distributions of a phosphor that is caused to luminescence by the excitation light, and to an optical tomographic information generating apparatus and a storage medium at which an optical tomographic information generating program is stored.

BACKGROUND ART

Methods of acquiring tomographic images of living bodies and the like include X-ray computed tomography (CT) using X-rays, ultrasound CT using ultrasound, NMR-CT employing nuclear magnetic resonance, proton CT using beams of particles such as protons, and so forth. It is known that living bodies are transmissive to light. Thus, optical CT using light for tomographic images of small animals has been proposed (for example, see Patent Reference 1: Japanese Patent Application Laid-Open (JP-A) No. 11-173976 and Patent Reference 2: JP-A No. 11-337476).

Light that is illuminated at a living body is scattered inside the living body, and the scattered light is emitted from the periphery of the living body. Optical CT detects light that is scattered and reflected in a living body and emitted from the periphery of the living body, acquires electronic signals, applies predetermined signal (image signal) processing to the respective electronic signals, and reconstitutes images from the obtained information. Thus, optical CT provides tomographic images of the living body.

In the field of pathological testing, a drug or the like containing a phosphor that emits light of a predetermined wavelength may be supplied into a living body and optical CT (hereinafter referred to as fluorescence CT) may be used when movements and distributions of the drug, concentration levels if the drug concentrates at particular locations, and the like are to be observed. That is, excitation light that excites the phosphor is illuminated onto the living body, light (fluorescence) that is emitted from the living body in response to this excitation light is detected, and two-dimensional tomographic images and a three-dimensional tomographic image of the living body are reconstituted. Hence, information on locations, quantities and the like of the phosphor or of a test drug, cells or the like containing the phosphor is obtained from the tomographic images.

In this fluorescence CT, the excitation light is illuminated at a point on the surface of the living body, and the scattered fluorescence emitted from the living body in consequence is detected at numerous points. The illumination position of the excitation light is altered and the process is repeated. Thus, data in the amount of the number of illumination points multiplied by the number of detection points is obtained. Relationships between these data items are established in accordance with distributions of the fluorescent material and scattering and absorption characteristics of light in the living body, and tomographic images may be reconstituted on the basis of these relationships.

When a concentration distribution of a phosphor is calculated in fluorescence CT in order to reconstitute a tomographic image, applying an inverse problem calculation to two light intensity distributions—the excitation light intensity distribution and the fluorescent light intensity distribution—has been proposed (for example, see Patent Reference 3: Description of U.S. Patent Application Publication Ser. No. 2007/0286468 and Non-patent Reference 1: S. R. Arridge, "Optical tomography in medical", Inverse Problems 15 (1999) R41-93).

In order to apply this proposal, it is necessary to detect both the excitation light intensity distribution and the fluorescent light intensity distribution. Therefore, an apparatus configuration capable of handling respective wavelengths of the excitation light is needed, and the inverse problem calculation needs to be carried out for two systems in order to obtain the respective light intensity distributions. This inverse problem calculation imposes a larger calculation load than a forward problem calculation and requires more time to calculate.

DISCLOSURE OF INVENTION

Technical Problem

The present invention has been made in consideration of the situation described above, and an object of the present invention is to provide a method for generating optical tomographic information that promotes simplification of an apparatus structure for fluorescent CT and moderation of a processing load for forming a tomographic image representing a distribution of a phosphor. A further object of the present invention is to provide an optical tomographic information generation apparatus and a storage medium storing an optical tomographic information generating program that are capable of forming a tomographic image representing a distribution of a phosphor in fluorescent CT.

Solution to Problem

In order to achieve these objects, the present invention includes: setting beforehand a diffusion coefficient and an absorption coefficient of a subject with respect to excitation light that, by being illuminated at a phosphor inside the subject, is capable of causing luminescence, and an absorption coefficient of the phosphor according to a concentration distribution of the phosphor; illuminating the excitation light from a light source toward a surface of the subject; detecting, at a periphery of the subject, intensities of fluorescence that is caused to be emitted from the phosphor by the excitation light illuminated at the subject and is emitted from the subject, and acquiring measurement data; acquiring a difference between fluorescence intensities and the measurement data, the fluorescence intensities being obtained from a mathematical model based on the diffusion coefficient and absorption coefficient of the subject and the absorption coefficient according to the phosphor concentration distribution that have been set beforehand and the excitation light emitted from the light source; updating the absorption coefficient of the phosphor so as to reduce the difference and repeating the acquiring of the difference; and on the basis of a concentration distribution of the phosphor acquired from the absorption coefficient of the phosphor, generating optical tomographic information that forms an optical tomographic image of the subject.

According to this invention, the intensities of the fluorescence emitted from the subject due to the excitation light being illuminated at the subject from the light source are detected, and the measurement data of the intensities of the fluorescence (fluorescence intensities) is acquired. Meanwhile, the scattering coefficient and the absorption coefficient of the subject are set beforehand, the absorption coefficient of the phosphor is provisionally set on the basis of a concentration distribution of the phosphor, and the intensities of the fluorescence are acquired from a mathematical model.

The fluorescence intensities acquired from the mathematical model and the fluorescence intensities obtained as measurement data are compared, and a difference therebetween is evaluated.

At this time, if the difference is large, an absorption coefficient that reduces the difference is estimated by performing an inverse problem calculation, and the processing of comparing the fluorescence intensity based on the estimated absorption coefficient with the measurement data is repeated. Thus, the absorption coefficient according to the concentration distribution of the phosphor is specified.

Thus, the concentration distribution of the phosphor in the subject is found from the obtained absorption coefficient according to the concentration distribution of the phosphor, and optical tomographic information for forming an optical tomographic image of the subject is generated.

Therefore, because the inverse problem calculation using the optical scattering equation need only be applied to the fluorescence intensities in order to obtain the optical tomographic information, a processing load for generating the tomographic information may be moderated and a shortening of the processing duration may be promoted.

Moreover, because intensity measurements of light need only be performed for fluorescence emitted from the subject in order to form a tomographic image, a simplification of the apparatus and a shortening of the measurement duration may be promoted.

In this invention, the detecting may include changing an illumination position of the excitation light onto the subject by relatively moving the light source along the periphery of the subject and detecting intensities of the fluorescence for the respective illumination positions. In this case, a plurality of detection sections that detect the fluorescence may be disposed at the periphery of the subject at a spacing that is set beforehand, and the respective detection sections may relatively move with respect to the subject, integrally with the light source, and detect the intensities of the fluorescence.

Thus, a structure for detecting the fluorescence intensities may be simplified.

In this invention, the diffusion coefficient and the absorption coefficient of the subject that are set beforehand may be set on the basis of optical characteristics of the subject.

An optical tomographic information generating device that employs this invention may include: a reading section that reads measurement data of intensities of fluorescence that is caused to be emitted from a phosphor inside a subject by excitation light being illuminated toward the subject and is emitted from the subject; a calculation section that calculates intensities of fluorescence from a mathematical model using a diffusion coefficient and an absorption coefficient of the subject with respect to the excitation light, which are set beforehand, and an absorption coefficient according to a concentration distribution of the phosphor; an evaluation section that compares a difference between the fluorescence intensities obtained by the calculation section and the fluorescence intensities based on the measurement data, and evaluates whether or not the difference is within a predetermined range; an update section that, if the difference is evaluated as not being within the predetermined range, updates the absorption coefficient according to the phosphor concentration distribution so as to reduce the difference; a repeating section that performs calculation by the calculation section using the absorption coefficient according to the phosphor concentration distribution that has been updated by the update section, and evaluation by the evaluation section of the result of the calculation; and a generation section that, when the difference is evaluated as being within the predetermined range, generates optical tomographic information that provides an optical tomographic image of the subject, including a concentration distribution of the phosphor, from the absorption coefficient according to the phosphor concentration distribution which has been evaluated.

Further, the present invention may be achieved by using a storage medium storing an optical tomographic information generating program for causing a computer to function as: a reading section that reads measurement data of intensities of fluorescence that is caused to be emitted from a phosphor inside a subject by excitation light being illuminated toward the subject and is emitted from the subject; a calculation section that calculates intensities of fluorescence from a mathematical model using a diffusion coefficient and an absorption coefficient of the subject with respect to the excitation light, which are set beforehand, and an absorption coefficient according to a concentration distribution of the phosphor; an evaluation section that compares a difference between the fluorescence intensities obtained by the calculation section and the fluorescence intensities based on the measurement data, and evaluates whether or not the difference is within a predetermined range; an update section that, if the difference is evaluated as not being within the predetermined range, updates the absorption coefficient according to the phosphor concentration distribution so as to reduce the difference; a repeating section that performs calculation by the calculation section using the absorption coefficient according to the phosphor concentration distribution that has been updated by the update section, and evaluation by the evaluation section of the result of the calculation; and a generation section that, when the difference is evaluated as being within the predetermined range, generates optical tomographic information that provides an optical tomographic image of the subject, including a concentration distribution of the phosphor, from the absorption coefficient according to the phosphor concentration distribution which has been evaluated.

Advantageous Effects of Invention

According to the present invention as described above, because the absorption coefficient is set beforehand as well as the scattering coefficient of a living body (the subject), the inverse problem calculation need only be performed for the intensity of the fluorescence, and therefore, a processing load for generating optical tomographic information representing a region of the phosphor inside the subject may be moderated, and a shortening of a processing duration may be promoted. In addition, an intensity measurement of light for generating the optical tomographic information need be carried out only for fluorescence emitted from the subject, and therefore, the present invention has advantageous effects in that a simplification of apparatus and a shortening of measurement duration may be promoted.

BRIEF DESCRIPTION OF DRAWINGS

FIG. 6 is a flowchart illustrating an example of processing that acquires a concentration distribution of a phosphor.

BEST MODE FOR CARRYING OUT THE INVENTION

Figure 1:
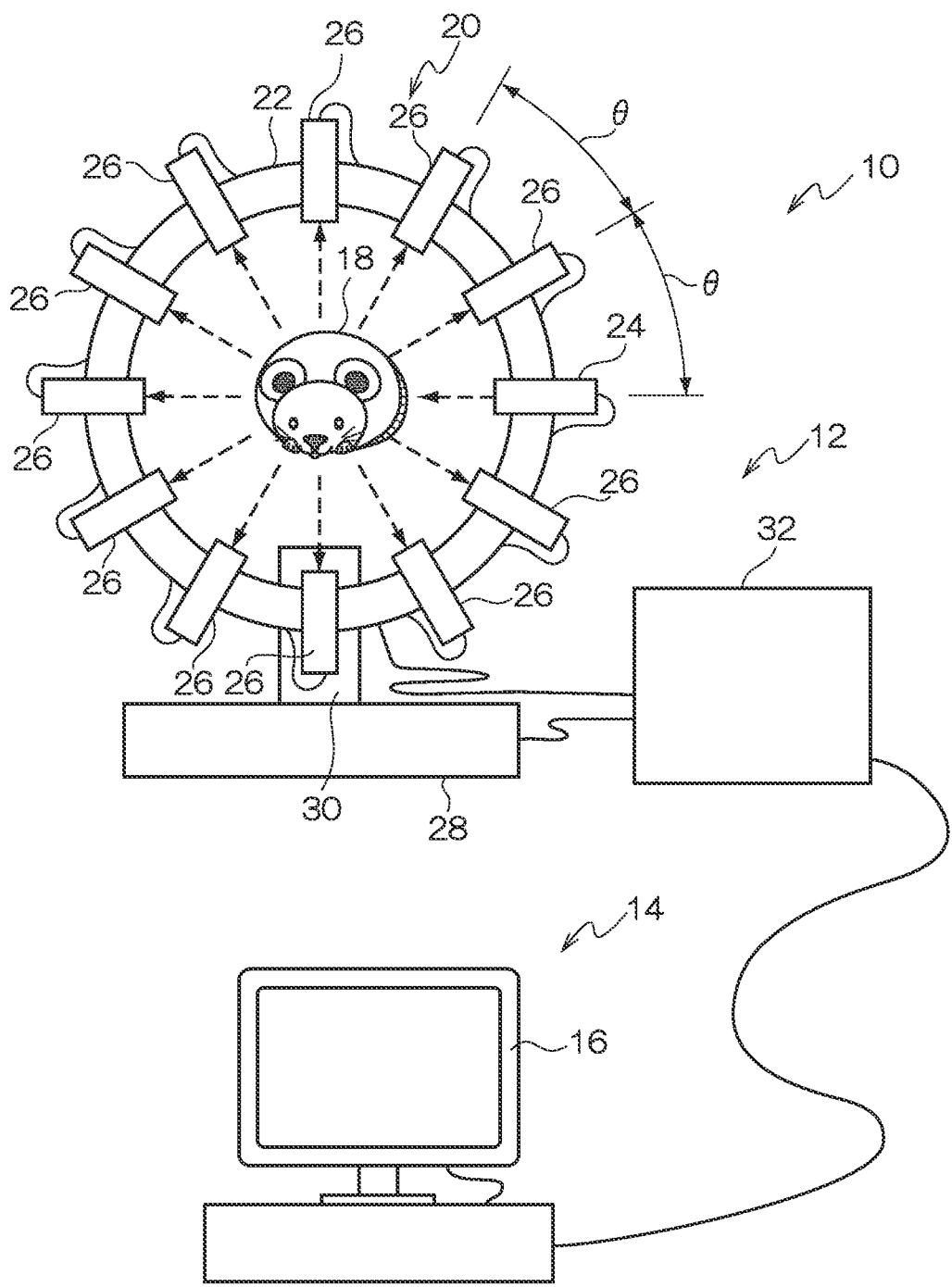
FIG. 1 is a schematic diagram illustrating an optical tomographic observation apparatus relating to an exemplary embodiment.

Herebelow, an exemplary embodiment of the present invention is described while referring to the attached drawings. FIG. 1 illustrates schematic structure of an optical tomographic observation apparatus 10 relating to the present exemplary embodiment. This optical tomographic observation apparatus 10 includes a measurement section 12 and an image forming section 14 that carries out image formation (signal processing) on the basis of electronic signals outputted from the measurement section 12. A monitor 16 such as a CRT, an LCD or the like is provided at the image forming section 14 to serve as a display section. Images based on measurement results from the measurement section 12 are displayed at the monitor 16.

At the optical tomographic observation apparatus 10, a living body such as a small animal or the like (for example, a nude mouse) serves as a subject 18 that is a target of observation. Images based on optical tomographic information obtained from the subject 18 (hereinafter referred to as optical tomographic images) are displayed at the monitor 16, and image data of the display images (optical topographic information) may be memorized at various kinds of memory medium.

The measurement section 12 is provided with a measurement unit 20. The measurement unit 20 is provided with a ring-shaped machine frame 22. An axial center portion of the machine frame 22 serves as a measurement position. In the measurement section 12, the subject 18 is disposed inside the machine frame 22, at the measurement position.

A light source head 24 which illuminates light of a predetermined wavelength toward the measurement position and plural light detection heads 26 which detect detected light, the detected light being light emitted from the subject 18, are mounted at the machine frame 22 with a predetermined angular spacing (offset at intervals of a predetermined angle θ). In the optical tomographic observation apparatus 10 employed in the present exemplary embodiment, as an example, eleven of the light detection heads 26 are arranged at intervals of 30° from the light source head 24 (i.e., θ=30°).

Thus, in the measurement section 12, detected light that is emitted from the subject 18 in response to the light illuminated from the light source head 24 may be detected in parallel by each of the eleven light detection heads 26.

The measurement section 12 is configured such that the machine frame 22 turns in steps of a predetermined angle about the center. Thus, in the measurement section 12, light is illuminated from the light source head 24 toward a plural number of points of a periphery of the subject 18, and the detected light may be detected at respective positions. As an example, the machine frame 22 is configured to turn in steps of the angle θ (θ=30°). In the measurement section 12, light is illuminated at twelve points of the periphery of the subject 18 and the detected light may be detected at eleven positions for each of the illuminated points. Note that the number of the light source head 24, the number of the light detection heads 26, the arrangement thereof, movement amounts of the light source head 24 and the light detection heads 26, and so forth are not limitations. Arbitrary numbers, arrangements and movement amounts may be employed, and a structure in which the light source head 24 and the light detection head 26 are made integral may be employed.

In the measurement section 12, a support pillar 30 is provided standing on a pedestal 28, and the machine frame 22 is turnably supported on the support pillar 30. The support pillar 30 is supported on the pedestal 28 to be translatable along the axial direction of the machine frame 22 (the direction between the front and rear surfaces of the paper of FIG. 1). Thus, in the measurement section 12, the machine frame 22 both is turnable and is moving along the axial direction thereof. Thus, measurements may be taken at arbitrary locations of the subject 18 in the axial direction of the machine frame 22.

A turning mechanism and a moving (translating) mechanism of this machine frame 22 may employ arbitrary structures. In the measurement section 12, the machine frame 22 is configured so as to turn but this is not a limitation. A structure is possible in which the subject 18 disposed inside the machine frame 22 turns, or both the subject 18 and the machine frame 22 may be turned.

Figure 2:
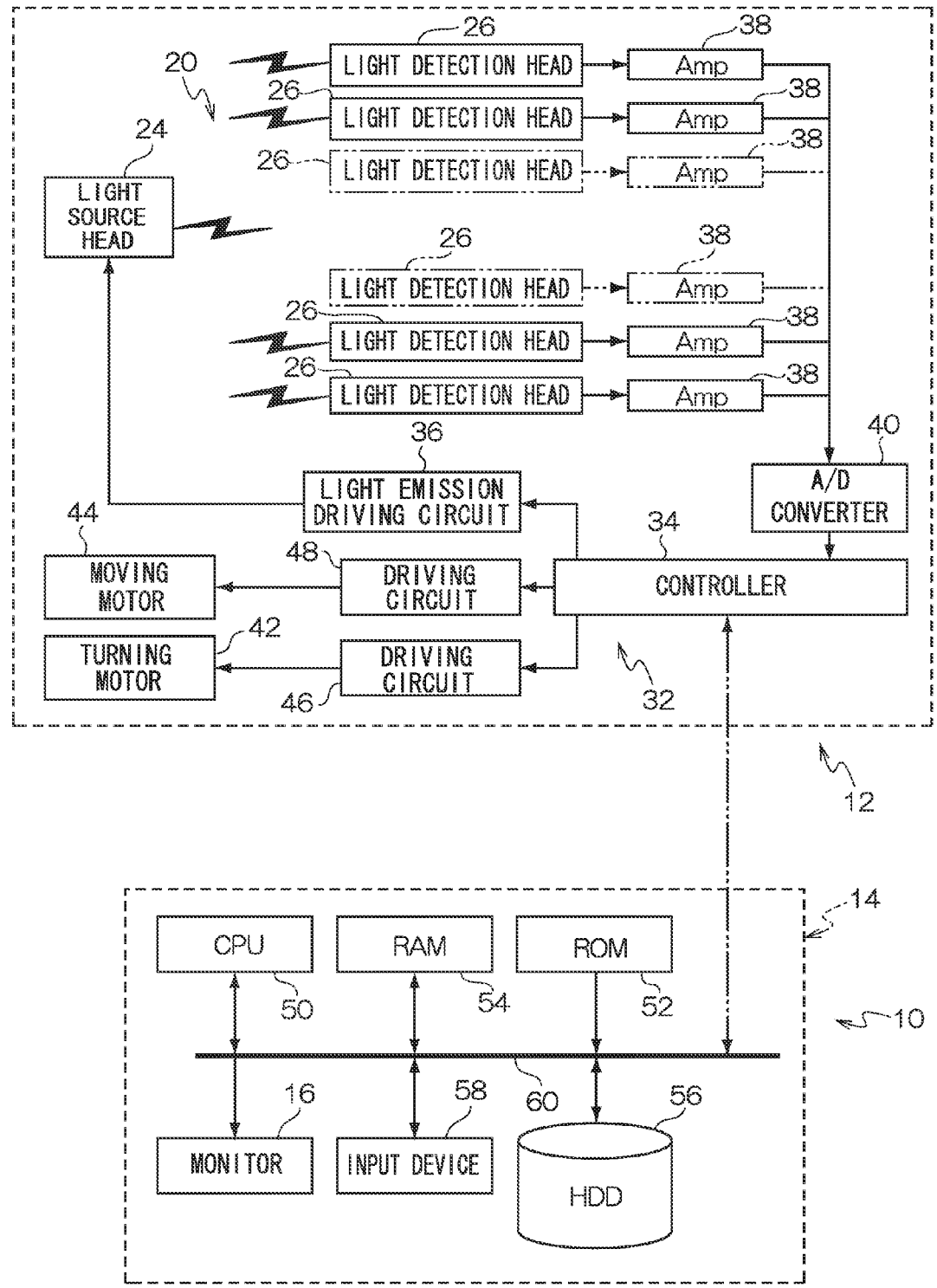
FIG. 2 is a schematic structural diagram illustrating a control section of the optical tomographic observation apparatus.

A control unit 32 is provided at the measurement section 12. As illustrated in FIG. 2, the control unit 32 is provided with a controller 34 that is constituted to include a microcomputer. The control unit 32 is provided with, for example, a light emission driving circuit 36 that drives the light source head 24, amplifiers (amps) 38 that amplify respective electronic signals outputted from the light detection heads 26, and an analog-to-digital (A/D) converter 40 that converts the electronic signals outputted from the amps 38 to digital signals. In the control unit 32, light emission from the light source head 24, the detection of detected light at the light detection heads 26, and the generation of measurement data representing intensities of the detected light that is detected are controlled by the controller 34.

The measurement section 12 may further include a turning motor 42 that drives to turn the machine frame 22 of the measurement unit 20, a moving motor 44 that moves the machine frame 22 in the axial direction, and respective driving circuits 46 and 48. These are structured to be connected to the controller 34.

The image forming section 14 is formed by a computer with a usual structure in which a CPU 50, a ROM 52, a RAM 54, an HDD 56 that serves as a memory section, an input device 58 such as a keyboard and mouse or the like, the monitor 16 and the like are connected to a bus 60. Thus, in the image forming section 14, various kinds of control, signal processing, image formation and the like may be carried out on the basis of a program memorized in the ROM 52, the HDD 56 or the like, or of a program memorized in an unillustrated removable memory or the like.

Exchanges of control signals and exchanges of data may be implemented between the image forming section 14 and the measurement unit 20 of the measurement section 12. For this structure, an arbitrary communications interface may be used.

Figure 3:
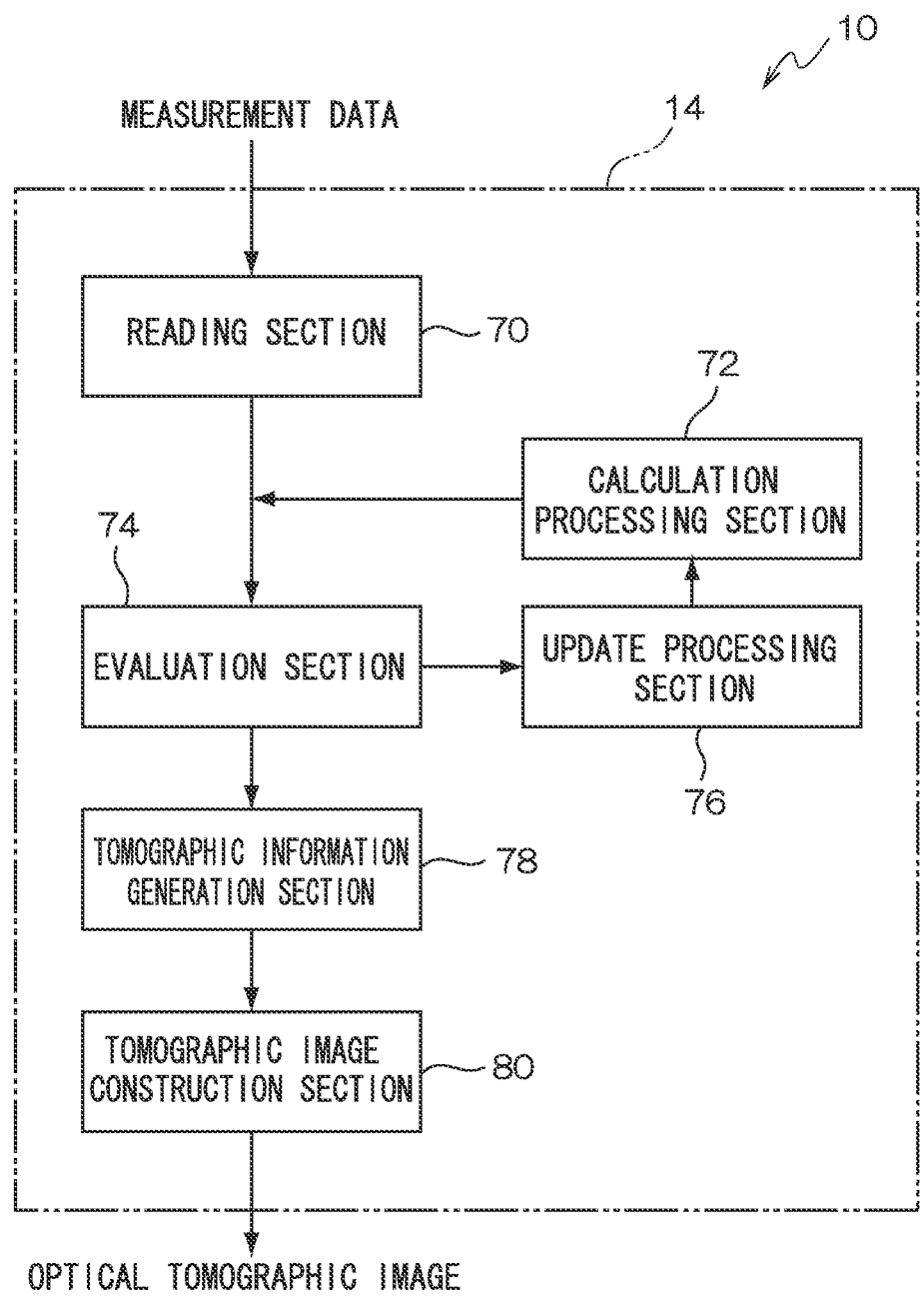
FIG. 3 is a functional block diagram illustrating an example of structure of an image forming section.

As illustrated in FIG. 3, a reading section 70 is formed at the image forming section 14. The reading section 70 reads measurement data outputted from the measurement section 12 (the measurement unit 20) while measurements of the subject 18 are being controlled by the measurement section 12. A calculation processing section 72, an evaluation section 74, an update processing section 76, a tomographic information generation section 78 and a tomographic image construction section 80 are formed at the image forming section 14.

At the calculation processing section 72, intensities of the fluorescence are calculated by a forward problem calculation using the optical scattering equation, on the basis of optical characteristic values that are set beforehand, including an absorption coefficient of the phosphor 62 with respect to light.

The evaluation section 74 evaluates a difference between the calculated fluorescence intensities and the fluorescence intensities obtained from the measurement data. From the fluorescence intensities, the update processing section 76 sets a light absorption coefficient according to a concentration distribution of the phosphor, such that the difference obtained from the results of evaluation by the evaluation section 74 is reduced by performing an inverse problem calculation of the optical scattering equation. At the calculation processing section 72, when the light absorption coefficient according to the phosphor concentration distribution is updated by the update processing section 76, the calculation processing section 72 performs a calculation of fluorescence intensities on the basis of the updated light absorption coefficient according to the phosphor concentration distribution.

This updating and evaluation of the fluorescence intensities is repeated. When, for example, it is evaluated that the calculated fluorescence intensities and the measurement data are matched, the tomographic information generation section 78 generates a phosphor concentration distribution, which is optical tomographic information, from the current absorption coefficient according to the phosphor concentration distribution. The tomographic image construction section 80 generates an optical tomographic image based on this optical tomographic information.

In this image forming section 14, predetermined data processing is applied to the measurement data read from the measurement section 12. Then, on the basis of the processing results, image processing is performed. Thus, an optical tomographic image of the subject 18 is reconstituted on the basis of the measurement data.

The generation of measurement data and the processing of the measurement data at the optical tomographic observation apparatus 10 are described.

In the optical tomographic observation apparatus 10 employed in the present exemplary embodiment, the light emitted from the light source head 24 serves as excitation light. A substance or drug containing a phosphor 62 (see FIG. 4A and FIG. 4B) that emits fluorescence in response to the illumination of this excitation light is supplied to the subject 18. In the optical tomographic observation apparatus 10, an image containing a distribution of the phosphor 62 in the subject 18 is reconstituted as a tomographic image of the subject 18, and the distribution of the phosphor 62 in various organs inside the subject 18 may be observed.

Figure 4A:
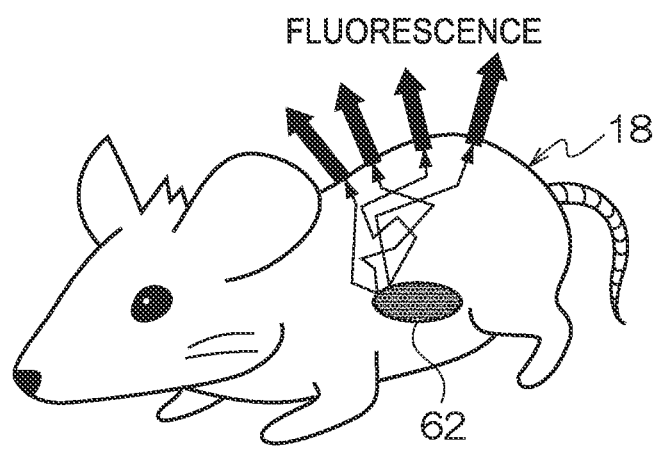
FIG. 4A is a schematic view illustrating the propagation of fluorescence within a living body.
Figure 4B:
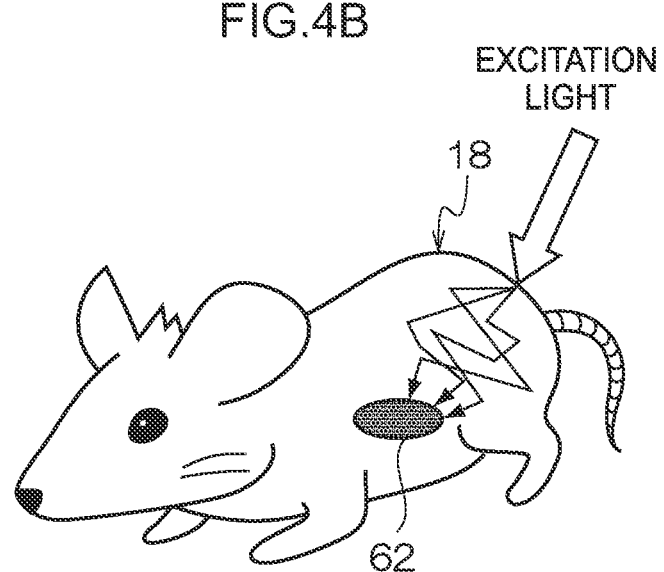
FIG. 4B is a schematic view illustrating the propagation of excitation light within the living body.

As illustrated in FIG. 4B, when the excitation light is illuminated onto the subject 18, the excitation light is scattered inside the subject 18 and reaches the phosphor 62. As a result, luminescence occurs at the phosphor 62 in the subject 18. As illustrated in FIG. 4A, the light emitted from the phosphor 62 (fluorescence) is repeatedly scattered in the subject 18 and is emitted from the subject 18. Here, both fluorescence and excitation light are emitted. However, at each light detection head 26, the fluorescence emitted from the subject 18 serves as the detected light and the light detection head 26 detects the intensity of this detected light (hereinafter referred to as fluorescence). The optical tomographic observation apparatus 10 obtains a distribution (a concentration distribution) of the phosphor 62 in the subject 18 from a light intensity distribution of this detected light.

When light such as the excitation light is illuminated at the subject 18, a region in the vicinity of an illuminated position acts as an anisotropic scattering region in which the refractive index for that light varies with orientation and the like, whereas a region where the light has advanced beyond a predetermined distance into the subject 18 acts as an isotropic scattering region.

If the light scattered in the subject 18 is considered as particles transporting energy, a distribution of light intensity may be represented using the optical transport equation, which is an expression of energy preservation of light intensity. However, this optical transport equation is currently difficult to solve.

In the subject 18, the anisotropic scattering region is ordinarily of the order of several millimeters. Therefore, in a subject 18 whose size is several centimeters or more, the interior of the body may be considered to be a substantially isotropic scattering region. That is, the scattering of light in the subject 18 may be approximated to isotropic scattering.

Therefore, a distribution of optical intensity can be obtained by using the optical scattering equation. The optical scattering equation is represented by expression (1), in which $\Phi(r,t)$ represents an optical density of the interior of the subject 18, $D(r)$ represents a diffusion coefficient, $\mu_a(r)$ represents an absorption coefficient, $q(r,t)$ represents the optical density of the light source, r represents a coordinate position in the subject 18, and t represents time.

$$\left\{ \frac{1}{c}\frac{\partial \phi}{\partial t} - \nabla \cdot D(r)\nabla + \mu_a(r) \right\}\Phi(r, t) = -q(r, t) \quad (1)$$

Here, the diffusion coefficient $D(r)$ has a relationship in a three-dimensional model $D(r)=[3\cdot\mu s'(r)]^{-1}$. In the present exemplary embodiment, which is a two-dimensional model, $D(r)$ has the relationship $D(r)=[2\cdot\mu s'(r)]^{-1}$. The symbol $\mu s'$ represents a reduced scattering coefficient. The term reduced scattering coefficient represents a scattering coefficient in the isotropic scattering region of a material that includes an anisotropic scattering region and an isotropic dispersion region (an anisotropic scattering material). The only subject of the optical scattering equation is an isotropic scattering region. Therefore, the reduced scattering coefficient $\mu s'$ is used rather than a scattering coefficient that takes account of anisotropy.

If continuous light is used for optical tomography observations, the distribution of light intensity is constant regardless of time. Therefore, expression (1) of the optical scattering equation may be shown as expression (2). Hereafter, a case of using continuous light is described.

If the diffusion coefficient $D(r)$ and the absorption coefficient $\mu_a(r)$, which are optical characteristic values, are already known and a distribution of light intensity emitted from the subject 18 is to be found using the light scattering equation, it may be calculated as a forward problem. However, the light intensity distribution is already known, so finding an optical characteristic value of the subject 18 using the light scattering equation is an inverse problem calculation.

$$\{\nabla \cdot D(r)\nabla - \mu_a(r)\}\Phi(r) = -q(r) \quad (2)$$

The diffusion coefficient $D(r)$ and the absorption coefficient $\mu_a(r)$ of the subject 18 vary with wavelengths of light. Therefore, if the diffusion coefficient with respect to the wavelength of the excitation light is represented as $Ds(r)$ and the absorption coefficient as $\mu as(r)$, and the optical density of the light source is represented as qs(r), the optical scattering equation for the excitation light is represented by expression (3). Meanwhile, if the diffusion coefficient with respect to the wavelength of the fluorescence is represented as Dm(r) and the absorption coefficient as μam(r), and the optical density of the fluorescence as a light source is represented as qm(r), the optical scattering equation for the excitation light is represented by expression (4). Using an optical density Φs(r) of the interior of the subject 18, a quantum efficiency γ of the phosphor 62 and a molar extinction coefficient 8, the optical density of the fluorescence qm(r) may be represented by qm=γ·ε·N(r)·Φs(r). Therefore, expression (4) may be replaced with expression (5).

Accordingly, in related art, excitation light intensities and fluorescence intensities emitted from the subject 18 are measured and an intensity distribution N(r) of the phosphor 62 is obtained by performing inverse problem calculations therewith.

Intensity distributions N(r) of the phosphor 62 that are obtained thus are combined into a tomographic image. Hence, a distribution of the phosphor 62 inside the subject 18 may be viewed in optical tomographic images.

$$\{\nabla \cdot D_s(r)\nabla - \mu_{as}(r)\}\Phi_s(r) = -q_s(r) \quad (3)$$

$$\{\nabla \cdot D_m(r)\nabla - \mu_{am}(r)\}\Phi_m(r) = -q_m(r) \quad (4)$$

$$\{\nabla \cdot D_m(r)\nabla - \mu_{am}(r)\}\Phi_m(r) = -\gamma \epsilon N(r)\Phi_s(r) \quad (5)$$

Figure 5:
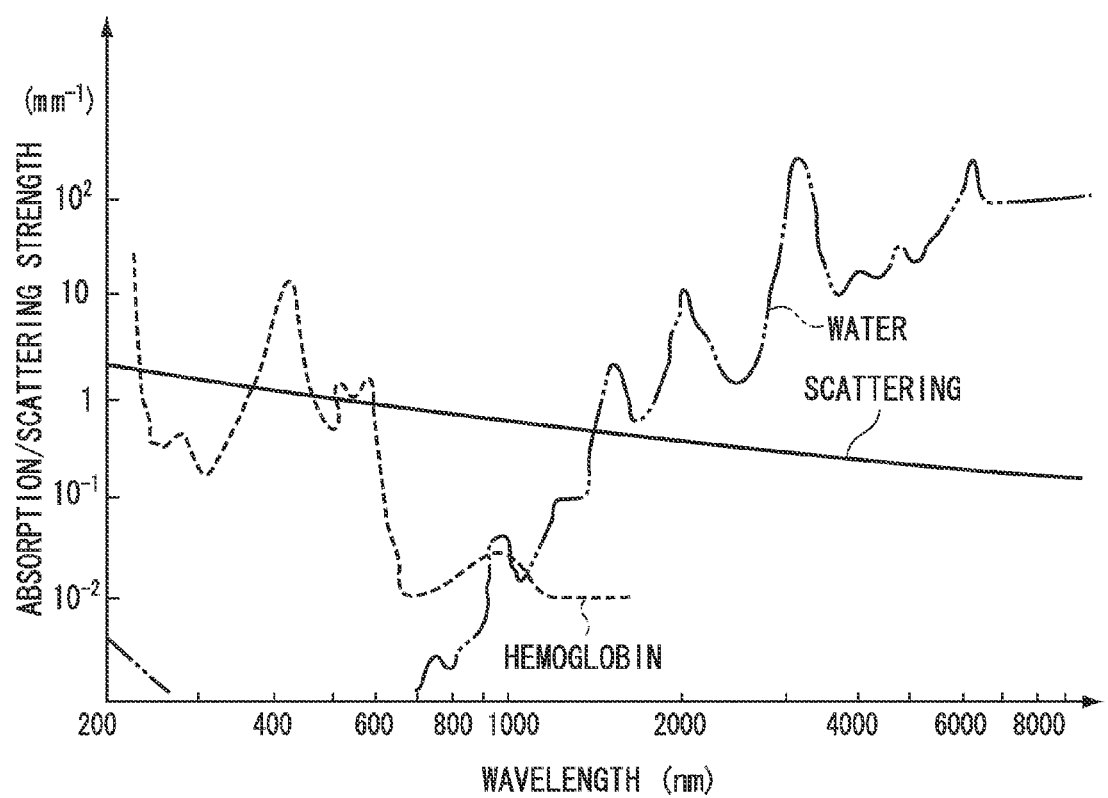
FIG. 5 is a graph illustrating an example of optical characteristics of a living body.

As illustrated by the broken line in FIG. 5, hemoglobin in the subject 18 strongly absorbs light with wavelengths less than around 700 nm, and as illustrated by the two-dot chain line in FIG. 5, water in the subject 18 strongly absorbs light with wavelengths above around 1 μm. Therefore, the wavelength region between 700 nm and 1 μm is a region in which absorption is weak, which is referred to as the optical window. In this wavelength region, the absorption coefficient μa of the subject 18 is in a range between 0.002 mm$^{-1}$ and 0.1 mm$^{-1}$.

The reduced scattering coefficient of light in the subject 18 μs' (the strength of scattering, which is illustrated by the solid line in FIG. 5) is smaller for longer wavelengths, and this change is gradual. In the wavelength region of 700 nm to 1 μm, the optical window, the strength of the scattering may be considered to be substantially constant.

Therefore, in the optical tomographic observation apparatus 10 employed in the present exemplary embodiment, infrared radiation (near infrared radiation) with a wavelength of between 700 nm and 1 μm corresponding to the optical window for the living body (the subject 18) is used as the light emitted from the light source head 24. Thus, the absorption coefficient μa and the reduced scattering coefficient μs' that are optical characteristic values of the subject 18, which is to say the diffusion coefficient D, may be substantially constant values (known values). Thus, in expression (3) and expression (5), Ds(r)=Dm(r)=D(r), μas(r)=μa(r)+ε·N(r), and μam(r)=μa(r). Herein, ε represents the molar extinction coefficient, N(r) represents the concentration distribution of the phosphor 62, and ε·N(r) represents absorption by the phosphor 62. Therefore, expression (3) and expression (5) may be replaced with expression (6) and expression (7).

$$\{\nabla \cdot D(r)\nabla - \mu_a(r) - \epsilon N(r)\}\Phi_s(r) = -q_s(r) \quad (6)$$

$$\{\nabla \cdot D(r)\nabla - \mu_a(r)\}\Phi_m(r) = -\gamma \epsilon N(r)\Phi_s(r) \quad (7)$$

A substance or drug containing the phosphor 62 that emits near infrared radiation as excitation light therefor is supplied to the subject 18 of which tomographic images are to be observed in the present exemplary embodiment.

As illustrated in expression (7), the intensity of fluorescence when the phosphor 62 acts as a light source is dependent on the intensity of the excitation light Φs(r). This is already known if the reduced scattering coefficient (diffusion coefficient) and absorption coefficient are set beforehand, and the optical intensity of the light source qs(r) is also known. Therefore, the optical intensity Φs(r) in the subject 18 may be found as a forward problem by a numerical analysis method such as the finite element method or the like.

Therefore, by measuring the intensity of fluorescence with the measurement section 12 and using this measurement data Φm(r), the concentration distribution N(r) of the phosphor 62 in the subject 18 is obtained by a single (one system) inverse problem calculation.

Herebelow, processing in the optical tomographic observation apparatus 10 and an example of processing in the image forming section 14 of the optical tomographic observation apparatus 10 is described.

In the optical tomographic observation apparatus 10, when the subject 18 is disposed in the measurement unit 20 of the measurement section 12, near infrared light of a wavelength set beforehand is illuminated from the light source head 24 onto the subject 18 as excitation light. This excitation light is dispersed in the subject 18 and propagated (transmitted).

If the phosphor 62 has been supplied to the subject 18, the excitation light is illuminated at the phosphor 62 and the phosphor 62 accordingly emits fluorescence. This fluorescence is dispersed in the subject 18 and propagated, and is emitted from the subject 18 to the periphery.

The light detection heads 26 are arranged in the measurement unit 20 at predetermined angular intervals so as to encircle the subject 18, and the fluorescence emitted from the subject 18 is detected by the light detection heads 26 as the detected light for the measurement section 12.

In the measurement section 12, the illumination position of the excitation light on the subject 18 and the detection positions of the fluorescence emitted from the subject 18 are relatively altered by turning of the machine frame 22, and the illumination of the excitation light and detection of the detected light are repeated. Thus, measurement data of intensities of fluorescence in response to excitation lights illuminated along the periphery of the subject 18 are obtained.

At the image forming section 14 of the optical tomographic observation apparatus 10, the concentration distribution N(r) of the phosphor 62 is calculated on the basis of this measurement data.

FIG. 6 illustrates an example of processing at this time. In the image forming section 14, near infrared radiation with a wavelength set beforehand according to optical characteristic values of the subject 18 serves as the excitation light. Therefore, the absorption coefficient μa(r) and the reduced scattering coefficient μs'(r) (or the diffusion coefficient D(r)) have been set beforehand and memorized at the image forming section 14. The absorption coefficient μa(r) and diffusion coefficient D(r) may be inputted to match up with the subject 18.

In this flowchart, first, in step 100, an initial value of the concentration distribution N(r) of the phosphor 62 is set. Then, in step 102, an intensity distribution Φm(r)calc of fluorescence emitted from the subject 18 is calculated on the basis of the set concentration distribution N(r) and the absorption coefficient μa(r) and diffusion coefficient D(r) that have been set beforehand. That is, a provisional fluorescence intensity distribution Φm(r)calc is obtained. This fluorescence intensity distribution Φm(r)calc may be easily calculated as a light scattering equation, which is a mathematical model, in the form of a known forward problem calculation using a numerical analysis method such as the finite element method or the like.

That is, the excitation light intensity distribution Φs(r)calc is obtained from expression (6) and expression (8), and a light intensity distribution combining the excitation light and the fluorescence light Φt(r)calc is obtained from expression (9). Hence, the fluorescence intensity distribution Φm(r)calc is obtained from the excitation light intensity distribution Φs(r)calc and the light intensity distribution Φt(r)calc (see expression (10)).

$$\{\nabla \cdot D(r)\nabla - \mu_a(r) - \epsilon N(r)\}\Phi_s(r) = -q_s(r) \quad (8)$$

$$\{\nabla \cdot D(r)\nabla - \mu_a(r)\}\Phi_t(r) = -q_s(r) \quad (9)$$

$$\Phi_m(r) = \gamma(\Phi_t(r) - \Phi_s(r)) \quad (10)$$

In step 104, the measurement data for the subject 18 that has been measured by the measurement section 12 is read in. Then, in step 106, a fluorescence intensity distribution (a fluorescence intensity distribution Φm(r)measure) is calculated from the read measurement data. That is, in step 106, the fluorescence intensity distribution Φm(r)measure is acquired on the basis of the measurement data.

Here, the fluorescence intensity distribution Φm(r)measure based on the measurement data is acquired after the calculation of the fluorescence intensity distribution Φm(r)calc is performed, but this is not a limitation. The fluorescence intensity distribution Φm(r)calc may be calculated after the fluorescence intensity distribution Φm(r)measure has been acquired.

Then, in step 108, the fluorescence intensity distribution Φm(r)measure based on the measurement data is compared with the fluorescence intensity distribution Φm(r)calc based on the calculation results and, in step 110, it is found whether the fluorescence intensity distribution Φm(r)measure and the fluorescence intensity distribution Φm(r)calc are matched. Whether or not the fluorescence intensity distribution Φm(r)measure and the fluorescence intensity distribution Φm(r)calc are matched may be judged from whether or not a difference therebetween is within a tolerance range that has been set beforehand.

If the fluorescence intensity distribution Φm(r)measure and the fluorescence intensity distribution Φm(r)calc are found not to be matched, the judgment of step 110 is negative and the image forming section 14 proceeds to step 112.

In step 112, a change in the optical intensity distribution in accordance with a change in optical characteristic values is calculated by a known method using a function matrix (a Jacobian matrix).

Then, in step 114, an error between the fluorescence intensity distribution Φm(r)measure and the fluorescence intensity distribution Φm(r)calc (for example, a second order error y) is evaluated using an inverse problem calculation with a mathematical optimization technique such as the Levenberg-Marquardt algorithm or the like. That is, the second order error y is obtained from expression (11), and this second order error y is evaluated.

$$y = \|\Phi_m(r)_{measure} - \Phi_m(r)_{calc}\|^2 \quad (11)$$

In step 114, an absorption εN of the fluorescence from the phosphor 62, that is, a concentration distribution N(r) of the phosphor 62, at which this second order error y is a minimum is estimated. This may be estimated by performing an inverse problem calculation using expression (7) or expression (12), which are the light scattering equation.

$$\{\nabla \cdot D(r)\nabla - \mu_a(r)\}\Phi_m(r) = -\gamma \epsilon N(r)\Phi_s(r) \quad (12)$$

When the concentration distribution N(r) is found in this manner, in step 116, the concentration distribution N(r) is updated on the basis of this calculation result.

The image forming section 14 repeatedly performs step 102 to step 116. Hence, when the fluorescence intensity distribution Φm(r)measure and the fluorescence intensity distribution Φm(r)calc are considered to be matched, the judgment in step 110 is positive and the image forming section 14 proceeds to step 118. The concentration distribution N(r) at this time is set as the concentration distribution N(r) obtained from the measurement data.

By comparison, in a related art structure, the diffusion coefficient D(r) and the absorption coefficient μa(r) are set as previously known values. Therefore, an excitation light intensity distribution Φx(r)measure is required as measurement data in addition to a fluorescence intensity distribution Φm(r)measure. In that case, inverse problem calculations are performed for both the light scattering equation with respect to the excitation light and the light scattering equation with respect to the fluorescence.

Thus, whereas it is necessary to find excitation light intensities and fluorescence intensities as measurement data in the related art structure, in the optical tomographic observation apparatus 10, measurement data of the excitation light intensities alone is sufficient. Therefore, the apparatus structure is simpler and a shortening of the measurement duration is promoted.

Furthermore, whereas the inverse problem calculation using the light scattering equation must be performed for two systems in the related art structure, in the image forming section 14 provided at the optical tomographic observation apparatus 10, the inverse problem calculation, which imposes a large processing load, need only be performed with one system, and rapid calculation is possible.

Herein, the present exemplary embodiment described above illustrates an example of the present invention and does not limit structures of the present invention. The present invention is not limited to the optical tomographic observation apparatus 10 and may be applied to optical tomographic observation apparatuses with arbitrary structures that illuminate excitation light at the subject 18, detect light emitted from the subject 18, and reconstitute tomographic images on the basis of light intensities thereof.

The invention claimed is:

1. A method for generating optical tomographic information comprising:
   setting beforehand a diffusion coefficient and an absorption coefficient based on optical characteristics of a subject that does not itself include a phosphor and provisionally setting a concentration distribution of the phosphor within the subject, wherein the subject is a target of observation after receiving the phosphor;
   detecting fluorescence, having a wavelength that is set according to the optical characteristics of the subject, which is emitted from the phosphor and emitted from the subject that is the target of observation toward a periphery of the subject, by illuminating excitation light, of the wavelength that is set according to the optical characteristics of the subject, from a light source toward a surface of the subject that is the target of observation, and acquiring measurement data of the intensities of fluorescence;
   acquiring a difference between fluorescence intensities and the measurement data, the fluorescence intensities being obtained based on a mathematical model using the diffusion coefficient and the absorption coefficient of the subject itself, the concentration distribution of the phosphor and intensities of the excitation light;

updating the concentration distribution of the phosphor so as to reduce the difference; and generating optical tomographic information, from which an optical tomographic image of the subject that is the target of observation that includes the concentration distribution of the phosphor is obtained, from the concentration distribution of the phosphor of which the difference is within a predetermined range.

2. The method for generating optical tomographic information according to claim 1, wherein: intensities of the fluorescence for the respective illumination positions are detected, while changing an illumination position of the excitation light onto the subject that is the target of observation by relatively moving the light source along the periphery of the subject that is the target of observation, and the measurement data is acquired.

3. The method for generating optical tomographic information according to claim 2, wherein a plurality of detection sections that detect the fluorescence are disposed at the periphery of the subject that is the target of observation at a spacing that is set beforehand, and the plurality of detection sections move integrally with the light source and detect the intensities of the fluorescence.

4. An optical tomographic information generating apparatus comprising:

a reading section that reads, as measurement data of intensities of fluorescence, a fluorescence of a wavelength that is set according to optical characteristics of a subject, by detecting the fluorescence which is emitted from a phosphor inside the subject and emitted from a periphery of the subject, by illuminating an excitation light, which is set according to the optical characteristics of the subject itself without the phosphor, toward the subject including the phosphor;

a calculation section that calculates intensities of fluorescence, which is emitted from the periphery of the subject including the phosphor, based on a mathematical model using a diffusion coefficient and an absorption coefficient of the subject itself without the phosphor which are set beforehand based on the optical characteristics of the subject itself, a concentration distribution of the phosphor, which is provisionally set with respect to the subject, and intensities of the excitation light;

an evaluation section that evaluates whether or not a difference between the fluorescence intensities obtained by the calculation section and the measurement data is within a predetermined range;

an update section that, if the difference is evaluated as not being within the predetermined range, updates the concentration distribution of the phosphor so as to reduce the difference; and a generation section that, when the difference is evaluated as being within the predetermined range with respect to a calculation result using the concentration distribution of the phosphor which is updated by the update section, generates optical tomographic information from which an optical tomographic image of the subject including the phosphor which includes the concentration distribution of the phosphor is obtained, from the concentration distribution of the phosphor which has been evaluated.

5. The optical tomographic information generating apparatus according to claim 4, further comprising a machine flame, at which a light source that emits the excitation light and a plurality of detection sections that detect the fluorescence are disposed along the periphery of the subject that is the target of observation at a spacing which is set beforehand, and wherein intensities of the fluorescence for respective illumination positions are detected, while changing an illumination position of the excitation light by relatively moving the light source and the plurality of detection sections integrally along the periphery of the subject that is the target of observation, by relatively moving the machine flame with respect to the subject that is the target of observation.

6. A non-transitory storage medium storing an optical tomographic information generating program for causing a computer to function as:

a reading section that reads, as measurement data of intensities of fluorescence, a fluorescence of a wavelength that is set according to optical characteristics of a subject, by detecting the fluorescence which is emitted from a phosphor inside the subject and emitted from a periphery of the subject, by illuminating an excitation light, which is set according to the optical characteristics of the subject itself without the phosphor, toward the subject including the phosphor;

a calculation section that calculates intensities of fluorescence, which is emitted from the periphery of the subject including the phosphor, based on a mathematical model using a diffusion coefficient and an absorption coefficient of the subject itself without the phosphor which are set beforehand based on the optical characteristics of the subject itself, a concentration distribution of the phosphor, which is provisionally set with respect to the subject, and intensities of the excitation light;

an evaluation section that evaluates whether or not a difference between the fluorescence intensities obtained by the calculation section and the measurement data is within a predetermined range;

an update section that, if the difference is evaluated as not being within the predetermined range, updates the concentration distribution of the phosphor so as to reduce the difference; and a generation section that, when the difference is evaluated as being within the predetermined range with respect to a calculation result using the concentration distribution of the phosphor which is updated by the update section, generates optical tomographic information from which an optical tomographic image of the subject including the phosphor which includes the concentration distribution of the phosphor is obtained, from the concentration distribution of the phosphor which has been evaluated.

* * * * *